United States Patent [19]

Wullbrandt et al.

[11] Patent Number: 5,010,012

[45] Date of Patent: Apr. 23, 1991

[54] PROCESS FOR THE ENZYMATIC PREPARATION OF OPTICALLY ACTIVE PHOSPHORUS CONTAINING FUNCTIONAL ACETIC ACID DERIVATIVES

[75] Inventors: Dieter Wullbrandt, Hofheim am Taunus; Reinhold Keller, Bad Soden am Taunus; Merten Schlingmann, Königstein/Taunus; Wolfgang Holla, Hofheim am Taunus; Manfred Schneider, Wuppertal, all of Fed. Rep. of Germany

[73] Assignee: Hoechst Aktiengesellschaft, Frankfurt am Main, Fed. Rep. of Germany

[21] Appl. No.: 231,290

[22] Filed: Aug. 12, 1988

[51] Int. Cl.⁵ .............................................. C12P 7/00

[52] U.S. Cl. .................................... 435/280; 435/135; 435/136

[58] Field of Search ........................ 435/280, 135, 136

[56] References Cited

U.S. PATENT DOCUMENTS

| 4,601,987 | 7/1986 | Klibanov et al. | 435/280 |
| 4,629,701 | 12/1986 | Sakimae et al. | 435/280 |
| 4,668,628 | 5/1987 | Dahod et al. | 435/280 |

Primary Examiner—Johnnie R. Brown
Assistant Examiner—Pamela S. Webber
Attorney, Agent, or Firm—Finnegan, Henderson, Farabow, Garrett, and Dunner

[57] ABSTRACT

Resolution of the racemates of phosphorus-containing functional acetic acid derivatives can be carried out in high yield and in enantiomeric purity using hydrolases such as esterases and lipases.

7 Claims, No Drawings

PROCESS FOR THE ENZYMATIC PREPARATION OF OPTICALLY ACTIVE PHOSPHORUS CONTAINING FUNCTIONAL ACETIC ACID DERIVATIVES

The racemic phosphorus-containing functional acetic acid derivatives described in EP 0,106,114 and EP 0,196,026 have excellent herbicidal and growth-regulating effects. As also known for many other optically active substances, with these compounds too only one enantiomer has the described effect or has higher activity. This is of course why there is interest in isolating the actual active substance from the racemic mixture. However, resolution of the racemate produced in the chemical synthesis is difficult by conventional methods such as, for example, diastereomeric salt formation and crystallization.

Resolution of racemates of proteinogenous amino acids using esterases and lipases or proteases has been described by Whitesides [Whitesides G.M., Wong C.H., Angew. Chemie 97, 617 (1985)].

It has now been found that the racemate of the phosphoruscontaining functional acetic acid derivatives can be resolved using hydrolases such as lipases and esterases. This is particularly surprising because these compounds do not occur in nature, and it was not to be expected, by reason of the substrate specificity of the enzymes used, that compounds of this type can be resolved according to the invention.

Hence the invention relates to a process for resolving racemates of compounds of the general formula I

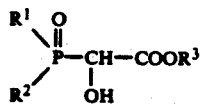

in which $R^1$ and $R^2$ are, independently of one another, $C_1$ to $C_4$ alkyl, and
$R^3$ is $C_1$ to $C_{18}$ alkyl,
which comprises incubation of the said compound in aqueous or aqueous-organic medium with an esterase and/or lipase. The invention also relates to the optically active compound obtainable by this process, as well as to the use of the compound as a herbicidal and growth-regulating agent for controlling weeds and in agriculture.

The invention is described in detail hereinafter, especially in its preferred embodiments. The invention is also defined in the patent claims.

The preparation of the compounds of the general formula I and of the corresponding acids is described in EP 0,106,114 and EP 0,196,026. The acids can be derivatized by conventional methods to give the corresponding esters. Suitable as substrate for the enzymatic conversion are compounds of the general formula I in which $R^1$ and $R^2$ can be, independently of one another, a $C_1$ to $C_4$ alkyl group, preferably a $C_1$ to $C_2$ alkyl group, and $R^3$ is an alkyl group having 1 to 18 carbon atoms, preferably 6 to 14 carbon atoms.

Suitable as hydrolase used to carry out the reaction according to the invention are lipases or esterases such as, for example, microbial lipases from Candida cylindiacea, Mucor miehei, Chromobacterium viscosum, or else esterases or lipases from porcine pancreas or porcine liver. However, the reaction is preferably carried out with porcine liver esterase and Candida cylindracea.

The enzymes can be added to the reaction mixture singly or together.

The hydrolase used according to the invention can be employed as a free, water-soluble enzyme or in a form insoluble in water, bound to a carrier by conventional methods (cf. German Offenlegungsschrift 2,732,301) in an aqueous or aqueous-organic solution. The concentration of substrate in the solution can vary within wide limits. No upper limit is placed on this. The concentration ranges used are preferably from 5 to 70%, in particular 20 to 50% and very particularly preferably 25 to 40%. It is still possible to carry out the reaction in lower concentration ranges, although at a slower rate. Suitable organic solvents which can be added to the reaction medium in order, for example, to increase the solubility of the substrate are solvents which are miscible with water and do not reduce the enzyme activity to an appreciable extent. Preferably used are alcohols such as methanol or ethanol, ketones such as acetone or methyl ethyl ketone, or tetrahydrofuran, dimethylformamide or dimethyl sulfoxide. The concentration of the solvent in the reaction solution should likewise be chosen such that the reduction in enzyme activity is inconsiderable, and it should preferably be about 5 to 15%. The reaction temperature is between 10° C. and 40° C., preferably between 15° C. and 35° C. The reaction time depends on the concentration of substrate and enzyme and on the enzyme activity and is 1 to 48 hours. Adequate enzymatic activity can be observed at a pH of about 5 to 9, preferably at about 6 to 8. The reaction can be carried out in a buffer or without addition of a buffer. If the enzyme is used in immobilized form, both batch and continuous processes are possible.

The final product obtained by the process according to the invention is the salt of the (+)-dialkylphosphinoylhydroxyacetic acid. The (−)-dialkylphosphinoylhydroxyacetic ester which is present racemizes immediately under the reaction conditions to give the (±) ester and can be subjected to renewed enzymatic resolution. This means that the (±) ester can be quantitatively converted into the salt of the (+) acid.

The process according to the invention is particularly preferably used for resolving the racemates of dimethylphosphinoyl-2-hydroxyacetic esters. The (+) enantiomer is obtained in large yield and has a high optical purity of 85-97% ee.

The final product of the process according to the invention has, by comparison with the corresponding racemate, twice the herbicidal and growth-regulating activity. It can be employed for the uses and in the formulations described in the Patent Applications EP 0,106,114 and EP 0,196,026. They are suitable for use both in agriculture and for controlling weeds.

The examples detailed hereinafter serve to explain the invention further. Unless otherwise indicated, percentage data relate to weight.

EXAMPLE 1

25 ml of 0.1 molar sodium phosphate buffer pH 7.0 were added to 4.98 g (30 mmol) of methyl (±)-dimethylphosphinoylhydroxyacetate, and the mixture was equilibrated at 25° C. The reaction was started by addition of 5 mg of porcine liver esterase, and the pH was maintained constant by addition of 1 normal sodium hydroxide solution. After 140 h (88% of the theoretical conversion), the reaction solution was filtered through Celite, washing with methanol. The solvent was removed in vacuo at no higher than 40° C., the residue was taken up in methanol, solids were removed by filtration, and the sodium (+)-dimethylphosphinoylhydroxyacetate was induced to crystallize in the cold.

Yield:

3.9 g of sodium (+)-dimethylphosphinoylhydroxyacetate

Specific rotation: $[\alpha]_D^{20} + 14.2°$ (c = 1.005 in methanol)

EXAMPLE 2

In analogy to Example 1, 2.36 g (10 mmol) of the (+)hexyl ester were dissolved in 25 ml of 0.1 molar sodium phosphate buffer and converted by addition of 5 mg of porcine liver esterase. After 150 hours (50.5% of the theoretical conversion) at a temperature of 25° C., the reaction was stopped.

Yield:

0.51 g of sodium (+)-dimethylphosphinoylhydroxyacetate (58% of theory based on reacted product)

Specific rotation: $[\alpha]_D^{20} + 18.6°$ (c = 1.059 in methanol)

EXAMPLE 3

In analogy to Example 1, 8.77 g (30 mmol) of the (±)decyl ester were dissolved in 25 ml of 0.1 molar sodium phosphate buffer pH 7.0 and incubated with 5 mg of porcine liver esterase for 19 hours (77% of the theoretical conversion).

Yield:

3.86 g of sodium (+)-dimethylphosphinoylhydroxyacetate (95% of theory based on reacted product)

Specific rotation: $[\alpha]_D^{20} + 20.4°$ (c = 1.0746 in methanol)

Enantiomeric purity: 86% ee.

EXAMPLE 4

In analogy to Example 1, 12.0 g (41 mmol) of the (+)decyl ester were dissolved in 25 ml of molar potassium phosphate buffer (pH 7.0) and incubated with 10 mg of porcine liver esterase for 19 hours (quantitative conversion).

Yield:

5.84 g of potassium (+)-dimethylphosphinoylhydroxyacetate (75% after recrystallization from methanol).

Specific rotation of $[\alpha]_D^{20} + 24.1°$ (c = 1.0043 in methanol)

Enantiomeric purity: 97% ee.

The enantiomeric purity was determined by proton resonance spectroscopy after diastereomeric salt formation with optically pure 1-phenylethylamine.

We claim:

1. A process for resolving the racemate of a compound of the formula I

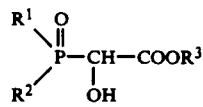

in which $R^1$ and $R^2$ are $C_1$ to $C_4$ alkyl, and $R^3$ is $C_1$ to $C_{18}$ alkyl, which comprises incubation of the said compound in aqueous or aqueous-organic medium with an esterase, lipase or esterase and lipase.

2. The process as claimed in claim 1, wherein incubation is carried out with a porcine liver esterase, a lipase from Candida cylindracea or a porcine liver esterase and a lipase from Candida cylindracea.

3. The process as claimed in claim 1, wherein the compound is present in the reaction medium in concentrations of 5 to 70%.

4. The process as claimed in claim 3, wherein the concentration is 20 to 50%.

5. The process as claimed in claim 1, wherein the reaction temperature is between 10° and 40° C.

6. The process as claimed in claim 5, wherein the reaction temperature is 15° to 35° C.

7. The process as claimed in claim 1, wherein the compound employed is a (±)-dimethylphosphinoylhydroxyacetic ester of the formula II

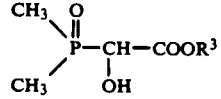

in which $R^3$ has the meaning mentioned in claim 1.

* * * * *